(12) United States Patent
Besier et al.

(10) Patent No.: US 12,226,163 B2
(45) Date of Patent: Feb. 18, 2025

(54) ORTHOPAEDIC PRE-OPERATIVE PLANNING SYSTEM

(71) Applicant: Formus Labs Limited, Auckland (NZ)

(72) Inventors: Thor Franciscus Besier, Auckland (NZ); Ju Zhang, Auckland (NZ); Antonije Velevski, Auckland (NZ)

(73) Assignee: Formus Labs Limited, Auckland (NZ)

( * ) Notice: Subject to any disclaimer, the term of this patent is extended or adjusted under 35 U.S.C. 154(b) by 374 days.

(21) Appl. No.: 17/620,291

(22) PCT Filed: Jun. 29, 2020

(86) PCT No.: PCT/IB2020/056143
§ 371 (c)(1),
(2) Date: Dec. 17, 2021

(87) PCT Pub. No.: WO2020/261249
PCT Pub. Date: Dec. 30, 2020

(65) Prior Publication Data
US 2022/0249168 A1 Aug. 11, 2022

(30) Foreign Application Priority Data

Jun. 28, 2019 (NZ) .......................... 755005
Apr. 20, 2020 (NZ) .......................... 736379

(51) Int. Cl.
*A61B 34/10* (2016.01)
*A61B 5/00* (2006.01)
(Continued)

(52) U.S. Cl.
CPC ............ *A61B 34/10* (2016.02); *A61B 5/0022* (2013.01); *A61B 5/1114* (2013.01);
(Continued)

(58) Field of Classification Search
CPC ..... A61B 34/10; A61B 5/0022; A61B 5/1114; A61B 5/4851; A61B 5/7264;
(Continued)

(56) References Cited

U.S. PATENT DOCUMENTS 10,258,256 B2  4/2019  Mahfouz
2010/0076563 A1*  3/2010  Otto ........................ G16H 20/30
623/20.14

(Continued)

FOREIGN PATENT DOCUMENTS

CN        109157286 A      1/2019
WO    WO 2012/113030 A1   8/2012
WO    WO 2018/067966 A1   4/2018

OTHER PUBLICATIONS

European Patent Office, Extended European Search Report, European Patent Application No. 20831426.0, Jul. 26, 2022, eight pages.

(Continued)

*Primary Examiner* — Md K Talukder
(74) *Attorney, Agent, or Firm* — WTA Patents

(57) ABSTRACT

A method for determining one or more of selection, positioning or placement of a surgical implant, the method includes:
predicting function of an impaired anatomical structure in an unimpaired condition;
predicting post-operative function of the structure for one or more implants;
selecting one or more of the implant, the implant position, or the implant location to improve the predicted post-operative function.

8 Claims, 18 Drawing Sheets

(51) Int. Cl.
*A61B 5/11* (2006.01)
*A61B 6/46* (2024.01)
*A61B 6/50* (2024.01)
*G06T 19/20* (2011.01)

(52) U.S. Cl.
CPC .......... *A61B 5/4851* (2013.01); *A61B 5/7264* (2013.01); *A61B 5/7275* (2013.01); *A61B 6/465* (2013.01); *A61B 6/468* (2013.01); *A61B 6/505* (2013.01); *G06T 19/20* (2013.01); *A61B 2034/104* (2016.02); *A61B 2034/105* (2016.02); *A61B 2034/108* (2016.02); *A61B 2562/0219* (2013.01)

(58) Field of Classification Search
CPC ....... A61B 5/7275; A61B 6/465; A61B 6/468; A61B 6/505; A61B 2034/104; A61B 2034/105; A61B 2034/108; A61B 2562/0219; G06T 19/20; G06T 2210/41; G06T 2219/004
See application file for complete search history.

(56) References Cited

U.S. PATENT DOCUMENTS

| | | | |
|---|---|---|---|
| 2013/0332128 A1* | 12/2013 | Miles | G16H 50/50 703/6 |
| 2016/0331463 A1* | 11/2016 | Nötzli | A61B 34/10 |
| 2017/0185713 A1* | 6/2017 | Bhatia | G16H 30/20 |
| 2017/0360358 A1* | 12/2017 | Amiot | A61B 5/686 |
| 2018/0008350 A1* | 1/2018 | Varadarajan | G16H 50/50 |
| 2018/0360544 A1* | 12/2018 | Vanheule | A61B 34/10 |
| 2019/0122330 A1* | 4/2019 | Saget | A61F 2/461 |
| 2019/0214126 A1* | 7/2019 | Goetz | A61B 6/563 |
| 2020/0030034 A1* | 1/2020 | Kontaxis | A61F 2/3094 |
| 2022/0249168 A1* | 8/2022 | Besier | A61B 5/7275 |

OTHER PUBLICATIONS

PCT International Search Report and Written Opinion, PCT Application No. PCT/IB2020/056143, Aug. 21, 2020, 21 pages.

* cited by examiner

Schematic of interactive 3D viewer

Example of the interactive viewer

ORTHOPAEDIC PRE-OPERATIVE PLANNING SYSTEM

TECHNICAL FIELD

This disclosure relates to the general field of planning an operative procedure, particularly an orthopedic procedure. Methods, systems, and devices for pre-operatively selecting and positioning implant components to use in operative procedures are also disclosed.

The disclosure is also related to methods, systems, and devices for pre-operatively planning joint-replacement surgery.

The disclosure is also related to methods, systems, and devices for measuring, predicting, and comparing patient joint function before and after joint-replacement surgery.

BACKGROUND

In orthopedic surgery, damaged or worn joints can be replaced with prosthesis or implants, for example hip implants, knee or shoulder implants amongst others. The primary aim of joint replacement surgery is to restore patient joint function. However, it is difficult to predict the functional impact of the selection and positioning of implants given variations in patient bone shape, muscle geometry and function, and movement styles for specific function tasks.

To perform a function task, e.g. lifting an object using one hand, a joint (e.g. shoulder) must rotate through a range of angles. A measure of the ability to perform the task is the magnitude of that range of angles. For example, a healthy subject may be able to rotate their shoulder in flexion 180 degrees while a patient requiring shoulder arthroplasty may only manage 90 degrees. It is the aim of the shoulder arthroplasty to restore that range of angles to 180 degrees or as much as possible through implant selection and placement.

This example is complicated by the variation in how each individual performs tasks. For example, due to differences in muscle strengths and natural preference, two individuals may perform a lifting task through different range of elbow and shoulder rotation. It may be unrealistic and unfavourable to the patient to try to restore their function based on the behaviour and ability of another.

Pre-operative surgery planning is often used to try to model the selection and positioning of implants. Combined with biomechanical models, one can try to help predict joint function. However, there are a number of problems that need to be addressed. At present the tools used by surgeons have limited ability to model the patient anatomy and limited ability to select and position different possible appropriate implants or prostheses.

Also, without knowledge of the patient's pre-operative joint function and what their function should be post-operatively, it is difficult to know what one should aim for when selecting and placing implants during pre-operative planning.

SUMMARY

It is an object of the present disclosure to provide a method, process or system for pre-planning or planning an orthopedic operative procedure, in particular an implant surgical procedure, which provides a viable or useful alternative to existing methods, processes or systems.

Implants can include without limitation permanent implants, e.g. artificial joint replacements, temporary implants used during surgery (e.g. surgical cutting guides), or implants that are bio-absorbed by the body over time after implantation.

We disclose a system and method for pre-operative surgical planning that collects, predicts, and analyses patient function in order to optimise the selection and placement of implants to maximise post operative joint function. This is performed in a patient-specific manner. The function is measured using a functional metric that can in one example be joint angle range, but can also use other quantitative values that capture the patient's range of motion. Although reference is made to joints, it will be appreciated that the disclosure is applicable to anatomical structures more generally including bones, ligaments, tendons and joints.

In one aspect the disclosure broadly provides a method for determining one or more of selection, positioning or placement of a surgical implant, the method including the steps of:
  Predicting function of an impaired anatomical structure in an unimpaired condition;
  Predicting post-operative function of the structure for one or more implants;
  Selecting one or more of the implant, the implant position or the implant location to improve the predicted post-operative function.

In an embodiment the selection includes minimising one or more differences between the predicted post-operative function and the predicted unimpaired function.

In an embodiment pre-operative data for the impaired structure is obtained. Data for the subject or patient may also be obtained, as may data for a population of subjects.

In an embodiment post-operative data may be obtained to improve the predictive functions.

In an embodiment the method includes producing a patient anatomical model. Preferably the model comprises a 3D model.

In an embodiment the model is generated from one or more patient medical images.

In an embodiment one or more patient medical images is processed and a statistical shape model is used to produce the patient anatomical model.

In an embodiment the method may include a machine learning method, such as an artificial neural network or a deep neural network for performing one or more method steps, for example classifying and/or filtering patient anatomical or medical images.

In an embodiment, the statistical shape model is used to identify or produce one or more of: an anatomical landmark, feature or region; one or more geometric models; one or more morphometric measurements.

The anatomical landmark(s), feature(s) or region(s) may be a surgically relevant landmark, feature or region. The surgically relevant landmark of feature may comprise a fixation point, or region or location for an implant.

The anatomical landmark(s), feature(s) or region(s) may be a relevant landmark, feature or region for determining a pre- or post-operative patient function, for example a a pre- or post-operative range of movement.

In another aspect the disclosure broadly provides a method for determining one or more of selection, positioning or placement of a surgical implant, the method including the steps of:
  obtaining pre-operative data for a patient having an impaired anatomical structure;
  predicting post-operative function of the anatomical structure for one or more implants;

selecting one or more of the implant, the implant position or the implant location to improve the predicted postoperative function of the structure.

The methods above may be applied to determine one or more of: the type of implant; the shape of the implant; the fixing points for the implant.

In an embodiment the method includes producing a patient anatomical model. Preferably the model comprises a 3D model.

In an embodiment the model is generated from one or more patient medical images.

In an embodiment one or more patient medical images is processed and a statistical shape model is used to produce the patient anatomical model.

In an embodiment the method may include a machine learning method, such as an artificial neural network or a deep neural network for performing one or more method steps, for example classifying and/or filtering patient anatomical or medical images.

In an embodiment, the statistical shape model is used to identify or produce one or more of: an anatomical landmark, feature or region; one or more geometric models; one or more morphometric measurements.

The anatomical landmark(s), feature(s) or region(s) may be a surgically relevant landmark, feature or region. The surgically relevant landmark of feature may comprise a fixation point, or region or location for an implant.

The anatomical landmark(s), feature(s) or region(s) may be a relevant landmark, feature or region for determining a pre- or post-operative patient function, for example a a pre- or post-operative range of movement.

In another aspect the disclosure provides a method or system for producing medical images for predicting unimpaired or post-operative function of anatomical structures.

In an embodiment the method includes producing a patient anatomical model. Preferably the model comprises a 3D model.

In an embodiment the model is generated from one or more patient medical images.

In an embodiment one or more patient medical images is processed and a statistical shape model is used to produce the patient anatomical model.

In an embodiment the method may include a machine learning method, such as an artificial neural network or a deep neural network for performing one or more method steps, for example classifying and/or filtering patient anatomical or medical images.

In an embodiment, the statistical shape model is used to identify or produce one or more of: an anatomical landmark, feature or region; one or more geometric models; one or more morphometric measurements.

The anatomical landmark(s), feature(s) or region(s) may be a surgically relevant landmark, feature or region. The surgically relevant landmark of feature may comprise a fixation point, or region or location for an implant.

The anatomical landmark(s), feature(s) or region(s) may be a relevant landmark, feature or region for determining a pre- or post-operative patient function, for example a a pre- or post-operative range of movement.

In another aspect the disclosure provides a graphical user interface for facilitating one or more of the foregoing methods.

In one embodiment the interface includes a 3D representation of patient anatomy and a proposed implant superimposed on the patient anatomy.

In one embodiment the 3D representation is manipulable to provide a plurality of view perspectives.

In one embodiment the interface shows implant or patient joint orientation in a plurality of different planes. Preferably the planes are orthogonal to each other.

In another aspect the disclosure provides apparatus for implementing the foregoing methods.

In one embodiment the apparatus comprises a client-server system.

In another aspect the disclosure provides a system for implementing the foregoing methods.

Further aspects will become apparent from the accompanying description.

DRAWING DESCRIPTION

One or more examples of a method and system for determining one or more of selection, positioning or placement of a surgical implant will be described below with reference to the accompanying drawings, in which.

Figure 3:
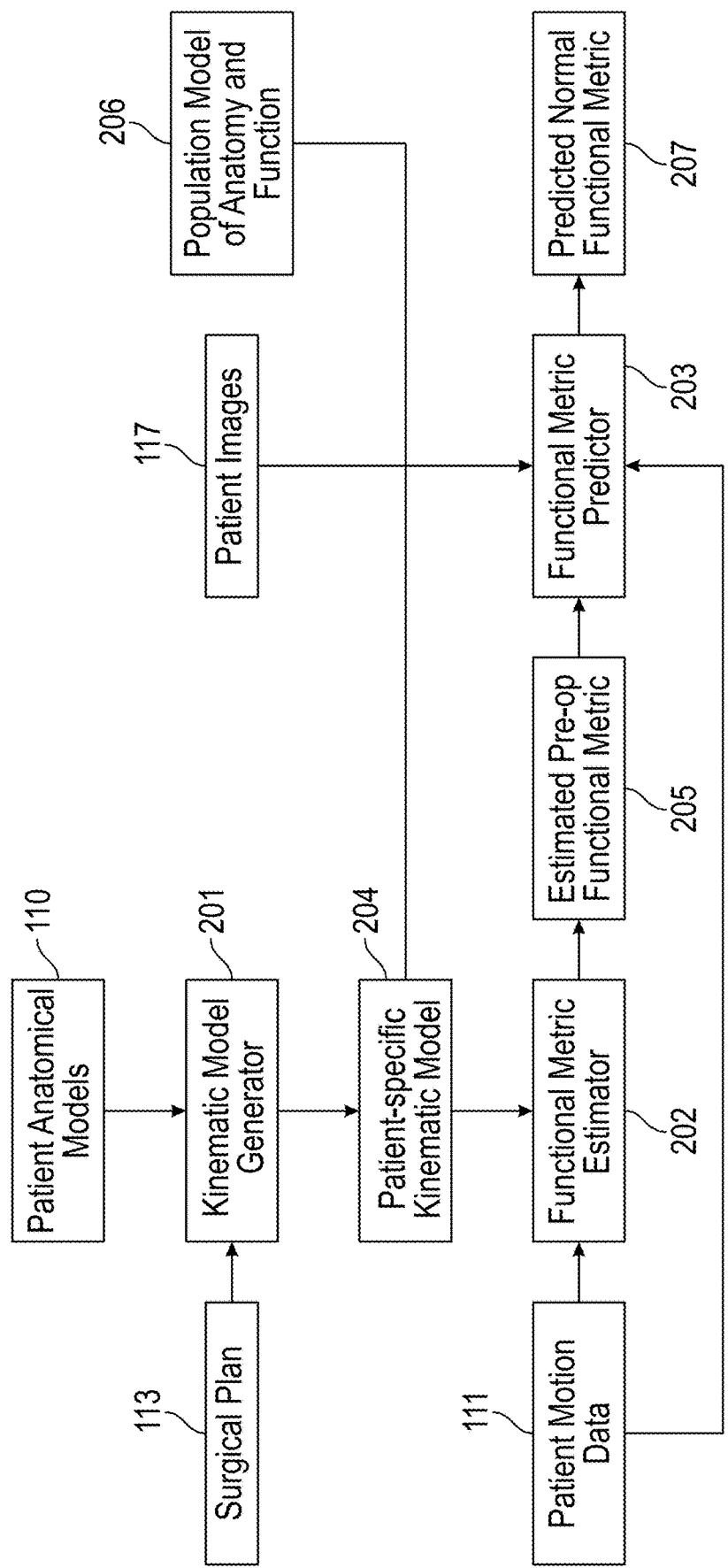
Figure 4:
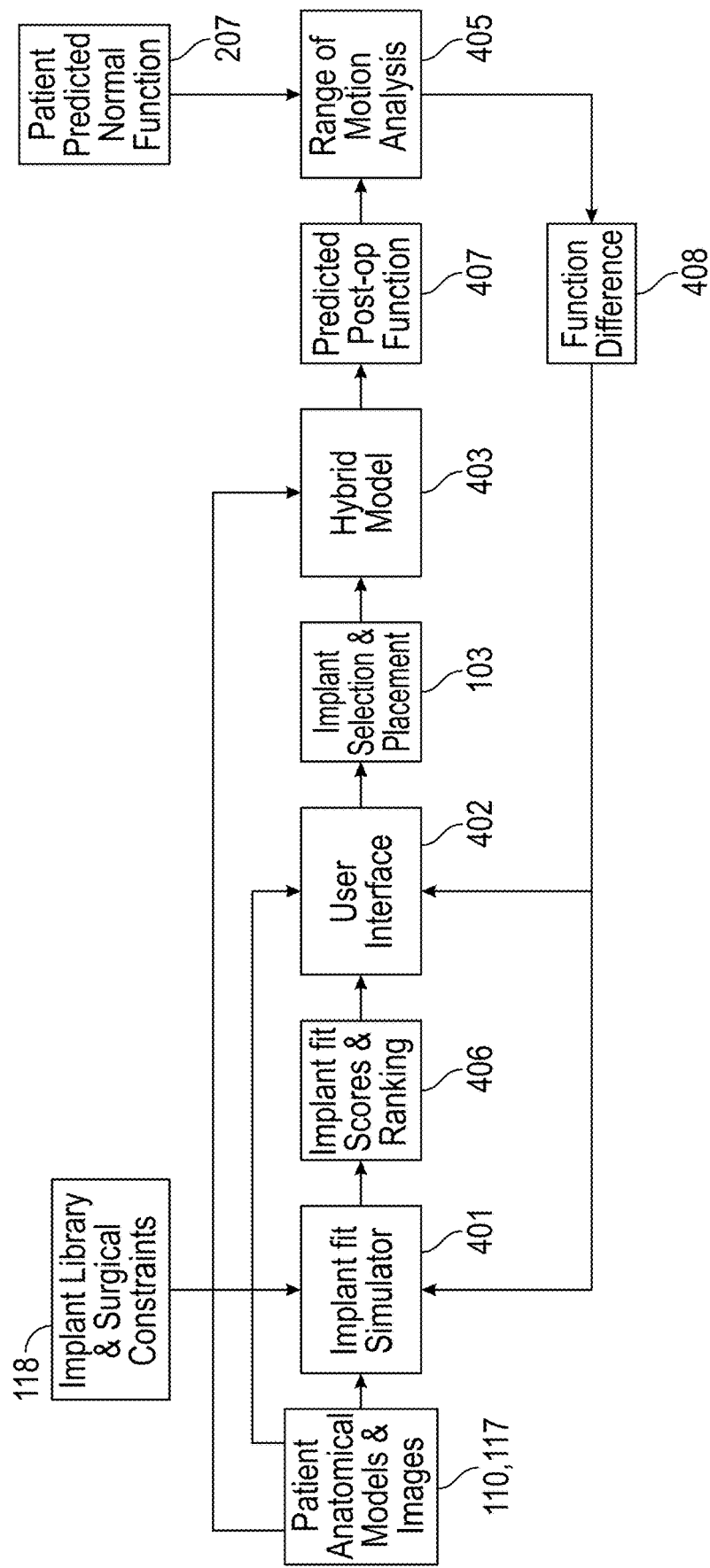
Figure 5:
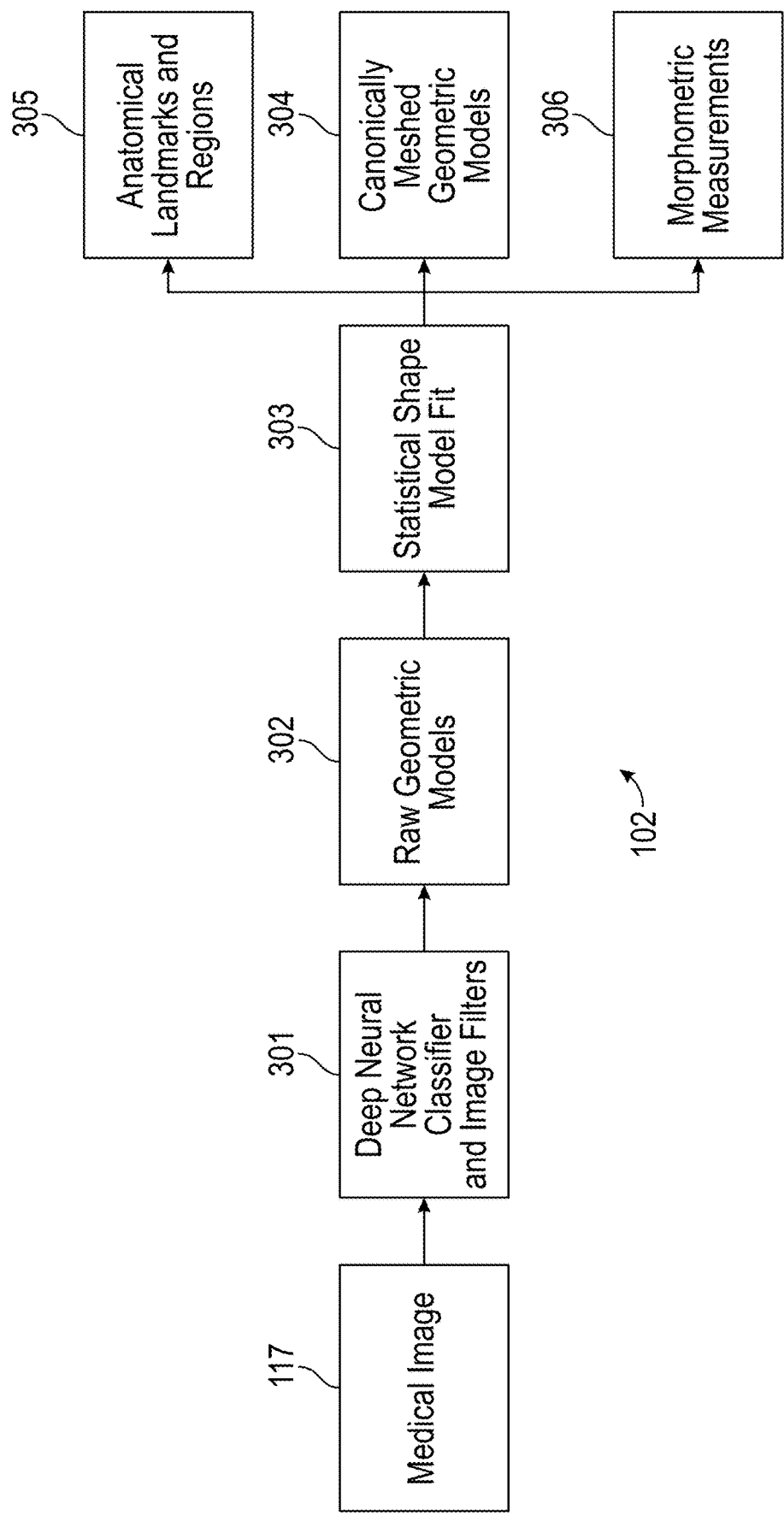
Figure 6:
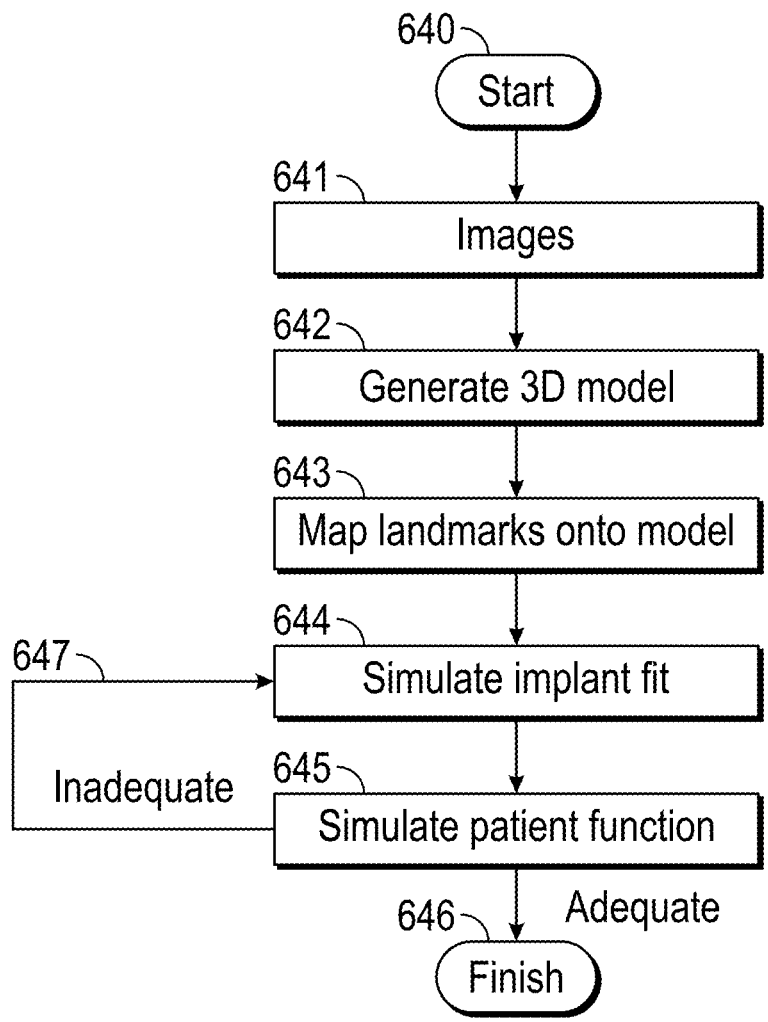
Figure 7:
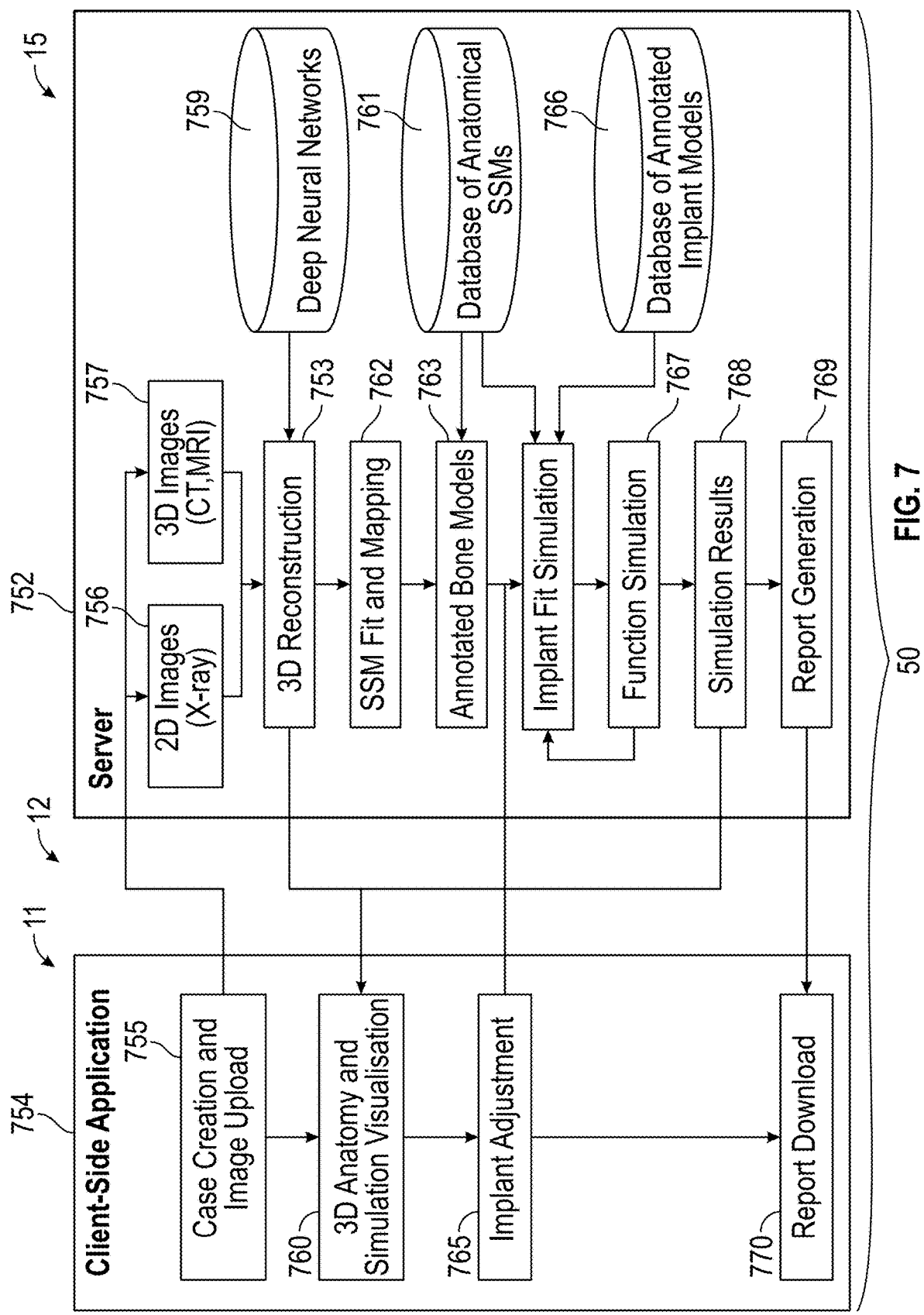
Figure 8:
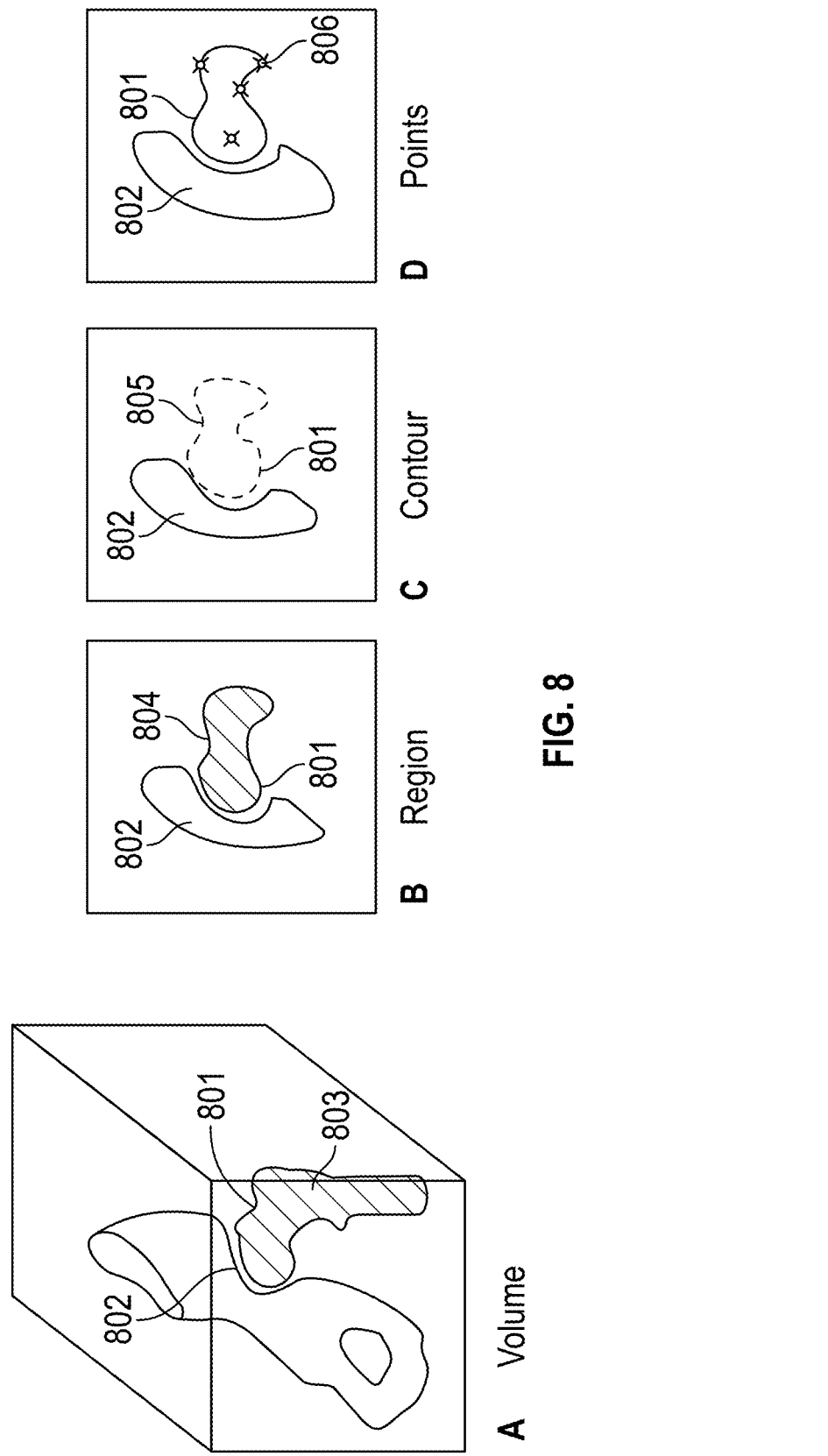
Figure 9A:
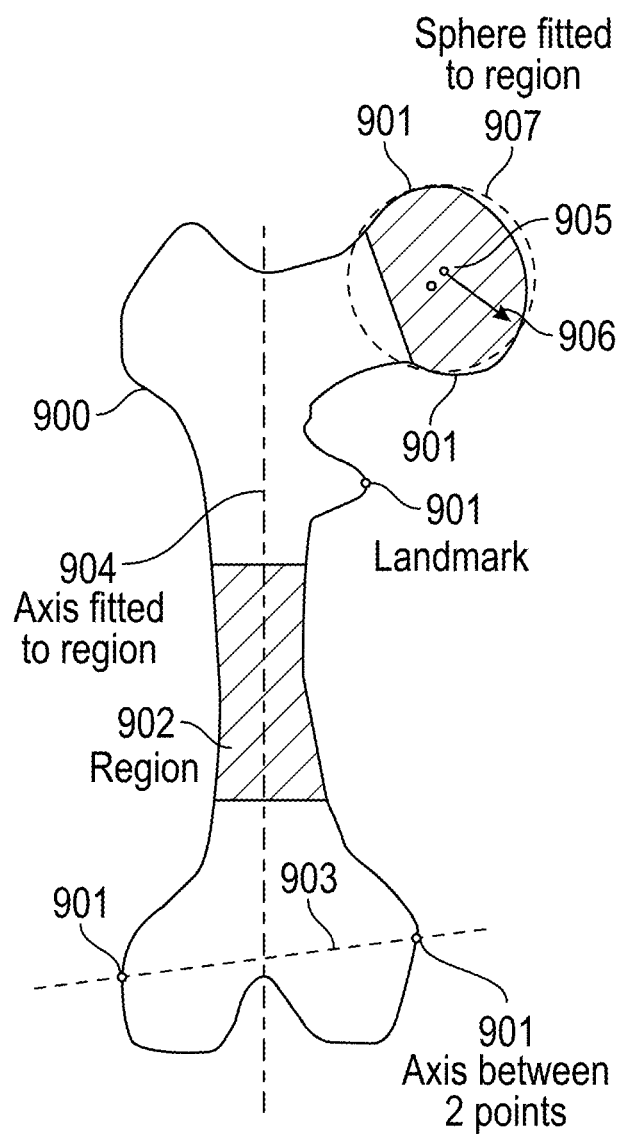
Figure 9B:
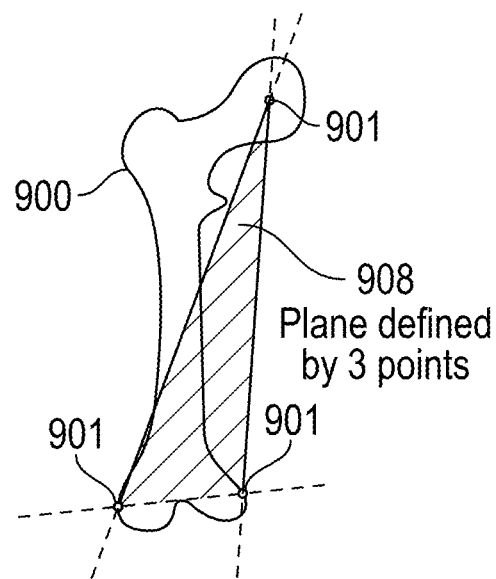

FIG. 3 is a diagram showing generation of a machine-learning/biomechanical hybrid model that predicts patient functional metrics FIG. 4 is a diagram of an implant and placement sub-system FIG. 5 is a diagram of an image processing sub-system FIG. 6 is a flow chart illustrating an example or embodiment of 3D model generation and simulation of implant fit and patient function FIG. 7 is a diagrammatic illustration of a client-server system providing an example of implementation of the invention FIGS. 8A-D are sketches showing examples of landmarks or geometric features that may be identified to form anatomical models FIGS. 9A and B are sketches showing examples of landmarks in the form of target surgical features for implant integration on the bone (or similar structures) in the model FIGS. 10-17 show examples of a Graphical User Interface to facilitate use of the system.

DETAILED DESCRIPTION

Specific examples or embodiments will now be disclosed with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description focuses on embodiments of the present invention applicable for planning an orthopedic procedure. The method includes positioning a virtual implant component relative to a digital model of the patient's anatomy. Embodiments of the invention will be described in the following with regard to planning a hip replacement procedure using a hip implant comprising an acetabular cup component and a femoral stem component. However, it will be appreciated that the invention is not limited to this application but may be applied to many other orthopedic procedures, such as joint implant procedures, e.g.

a knee implant procedure, an ankle implant procedure etc. wherein one or several implant components may be included in the procedure. For example, positioning a virtual implant component may comprise defining positional information for at least one of an affected femoral head, affected femoral shaft, unaffected femoral head, unaffected femoral shaft, a cup of a virtual implant, and a stem of a virtual implant. Those skilled in the art will understand that modelling of anatomical structures as disclosed herein is not limited to modelling bone (although this is used as a primary example), but includes other structures including without limitation connective tissue, ligaments, tendons, cartilage, muscles and vascular structures.

The tools used to preform pre-operative planning as disclosed herein are computer implemented. Accordingly, aspects of the present disclosure are implemented in a data processing environment.

Figure 1A:
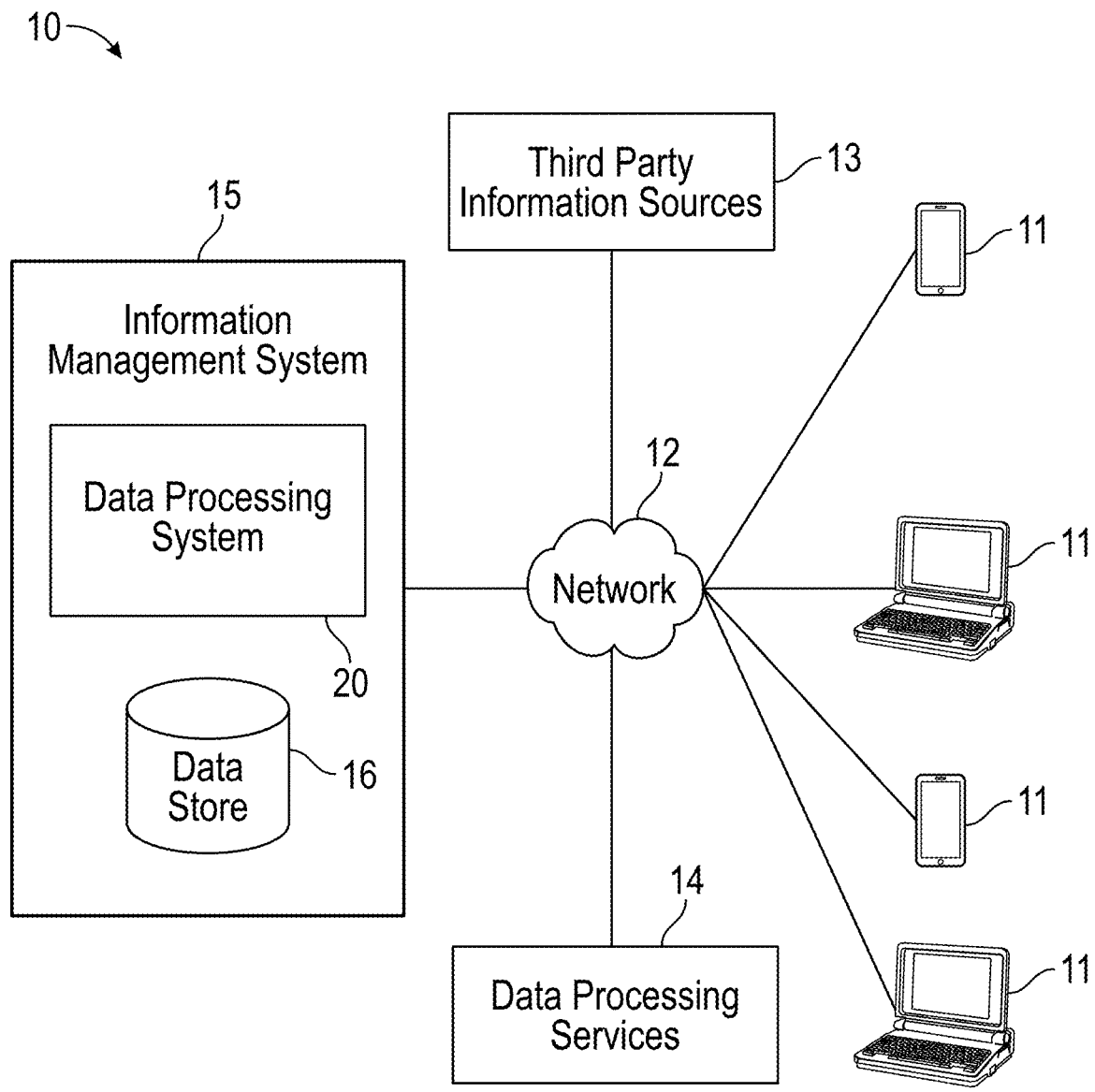
FIGS. 1A and 1B are diagrams showing apparatus including a processing environment for implementing the method and system disclosed herein.
Figure 1B:
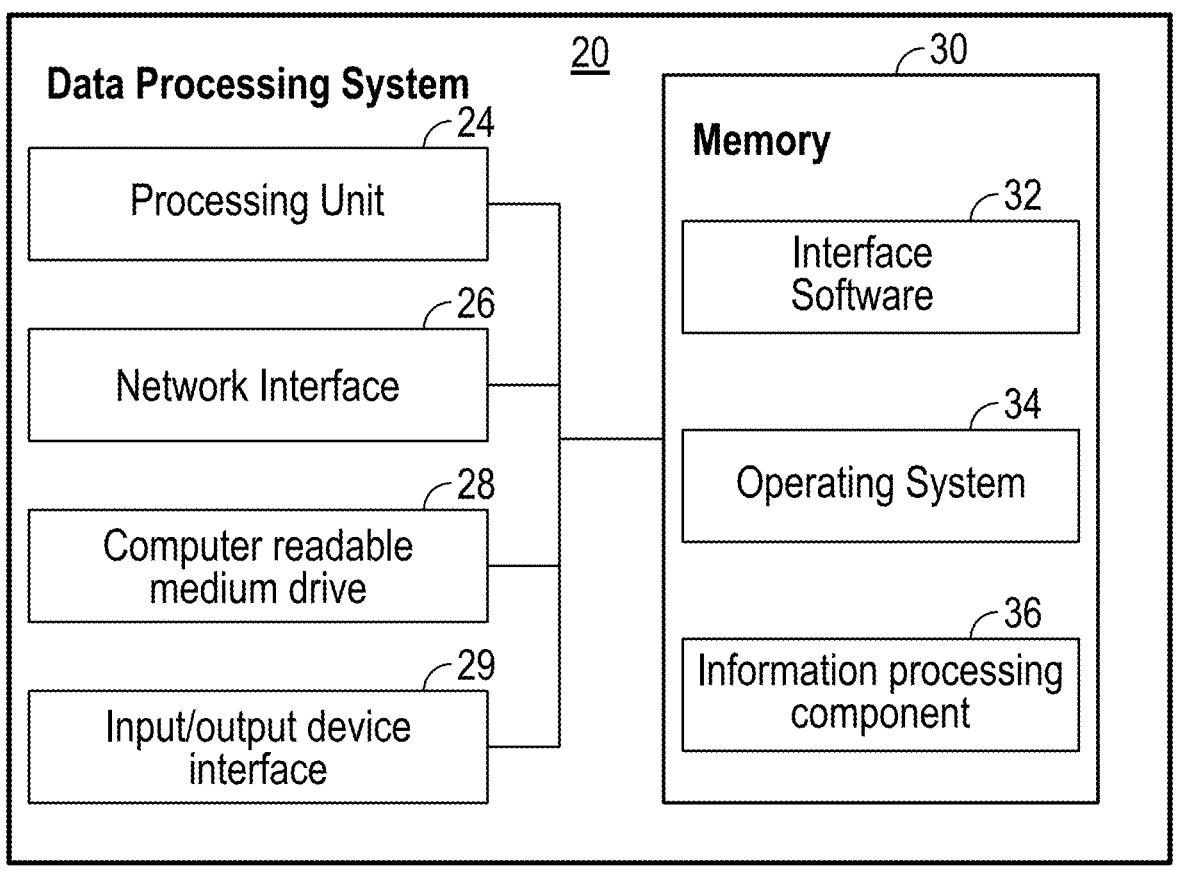

One or more aspects of the present disclosure are intended for use in a data processing environment, which will initially be discussed in broad terms with reference to FIGS. 1A and 1B of the drawings. Referring to FIG. 1A, a data processing network environment in which one or more embodiments of the present invention may be used is depicted. The data processing environment 10 may include a plurality of individual networks, such as wireless networks and wired networks. A plurality of wired and/or wireless devices 11 may communicate over a network 12 with third party information sources 13, data processing services 14 and information management system 15 which may include a data store 16 and a data processing system or computing device 20.

The computing device 20 is shown in more detail in FIG. 1B. The device 20 may be implemented as a microprocessor which can process data accessed from additional network based resources, such as web sites or other supplemental content delivery.

FIG. 1B depicts one embodiment of an architecture of illustrative computing device 20 for implementing various aspects of the data processing system or environment 10 in accordance with aspects of the present application. The data processing system 10 can be a part of the instantiation of a set of virtual machine instances. The computing device 20 may a stand-alone device that functions as the data processing system 10.

The general architecture of the device 20 depicted in FIG. 1B includes an arrangement of computer hardware and software components that may be used to implement aspects of the present disclosure. As illustrated, the device 20 includes a processing unit 24, a network interface 26, a computer readable medium drive 28, an input/output device interface 29, all of which may communicate with one another by way of a communication bus. The components of the computing device 20 may be physical hardware components or implemented in a virtualized environment.

The network interface 26 may provide connectivity to one or more networks or computing systems. The processing unit 24 may thus receive information and instructions from other computing systems or services via a network. The processing unit 24 may also communicate to and from memory 30 and further provide output information.

The memory 30 may include computer program instructions that the processing unit 24 executes in order to implement one or more embodiments. The memory generally includes RAM, ROM, or other persistent or non-transitory memory. The memory may store an operating system 34 that provides computer program instructions for use by the processing unit 24 in the general administration and operation of the device. The memory may further include computer program instructions and other information for implementing aspects of the present disclosure. For example, in one embodiment, the memory includes interface software 32 for receiving and processing requests from the client devices 11. Memory 30 includes an information match processing component 36 for processing the user interactions to create graphical interfaces as described herein.

Aspects of the present application should not be limited to interpretation requiring a physical, virtual or logical embodiment unless specifically indicated as such.

Figure 2:
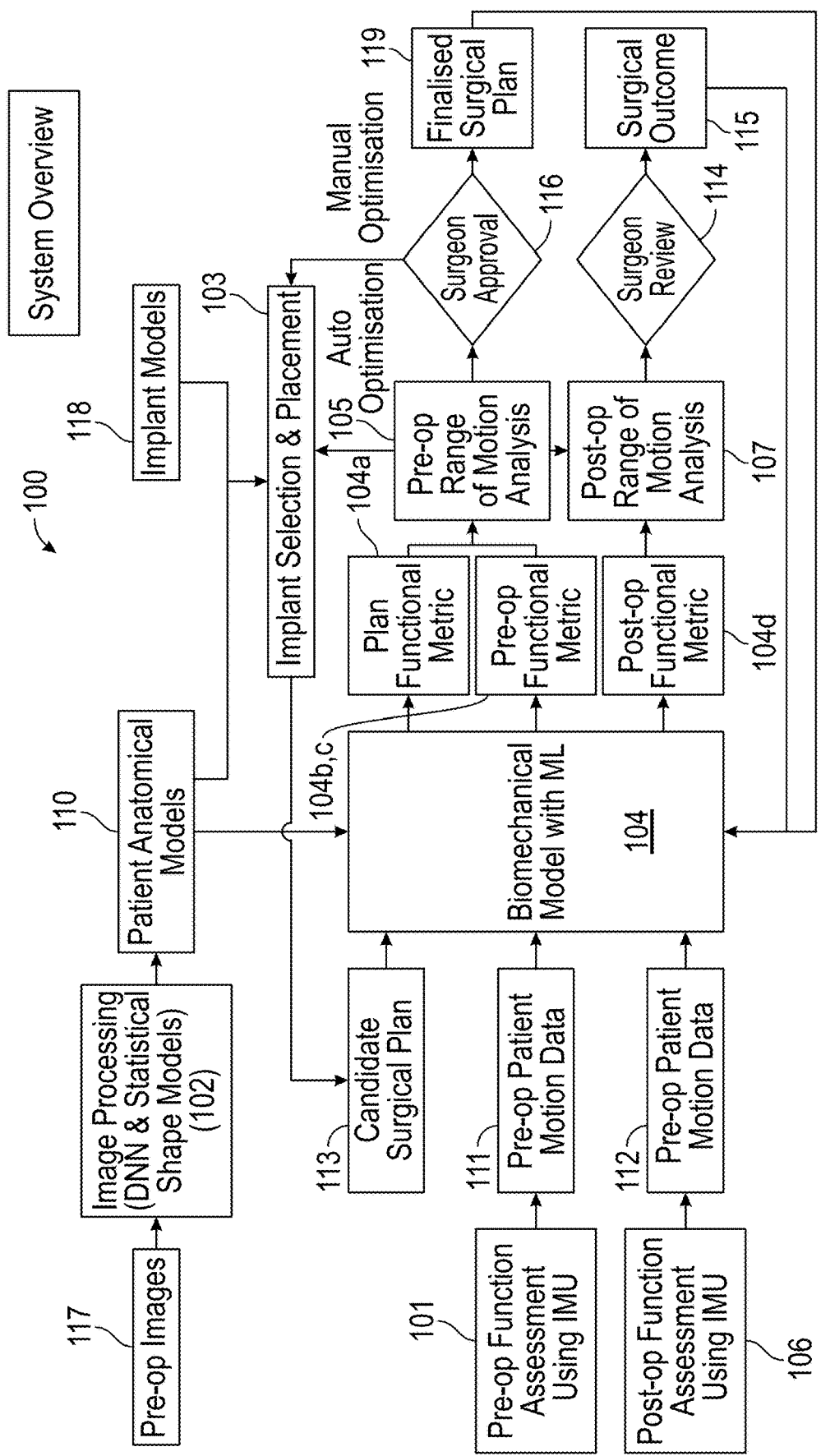
FIG. 2 is a diagrammatic system overview.

Referring to FIG. 2, an overall schematic of one embodiment of a system 100 for pre-operative planning is illustrated. Although this embodiment is described with reference to implants, those skilled in the art will appreciate that the system is applicable with other operative procedures.

The system is centered on the construction of a biomechanical model 104, which in at least some embodiments is implemented or augmented with machine learning, as will be described further below. Model 104 receives patient anatomical models 110 and an initial surgical plan 113, along with pre-operative patient motion data. This motion data comprises patient motion data 111 (derived from a pre-operative assessment 101), and patient motion data 112 (derived from an assessment of post-operative patient function 106).

The patient anatomical models are derived from pre-operative images 117 which are processed at 102 to provide models 110.

The outputs from the model 104 include functional metrics 104a for implementing a surgical plan, and pre- and post-operative functional metrics 104b,c,d. Pre-operative metrics 104b,c can be used to develop a pre-operative range of motion analysis 105 which can be used to determine implant selection and placement as shown in 103. Post-operative metrics 104d may be used to develop a post-operative range of motion analysis 107, which may be compared with the pre-operative analysis data 105 for optional review by a system user such as a surgeon at 114 before determining a surgical outcome 115 that may be provided to the model 104 as data for to improve future modelling and processing, for example through use of machine learning. In some embodiments the system can process data automatically with minimum input from a surgeon. This may depend on the nature or complexity of the operative procedure. In some embodiments, for example, the surgical procedure can be planned with no specific decisions needing to be taken by a surgeon. In some embodiments, the surgical plan may be provided in a machine readable form to enable a machine such as a robot to perform the surgical procedure.

In other embodiments the surgeon may be able to make manual selections based on data such as pre- or post-operative outcomes determined by the model 104.

Implant models 118 are provided to allow the system to perform the required modelling for placement of the implant as part of the procedure, and the post-operative outcomes.

Thus implant models 118 allow model 104 to produce data for placement of the implant relative to the patient anatomical structures and to allow visualisation of implant as required.

In some embodiments outcomes can be optimised automatically. For example, the implant selection and placement can be optimised automatically. This may occur by an an iterative process for example, so initial implant selection and placement data can be input into the surgical plan 113 and processed again in accordance with model 104 and this process may continue until a selection and placement is determined that falls within one or more threshold parameters. The threshold parameters may for example include some of the pre-operative and/or post-operative range of motion analysis data 105, 107.

In other embodiments a surgeon may use data from the pre-operative range of motion analysis 105 for example to try using a completely different form of implant at 103. Thus in the example shown in FIG. 2, the surgeon may have the option to approve or alter, at 116, the pre-operative range of motion analysis 105 and thus provide a manual adjustment, or iteration, or override for implant selection and placement 103.

A finalised surgical plan 119 can be produced as an output, and as can be seen from FIG. 2, data from the plan can be fed back as an input to the model 104 to allow the system to iteratively process all inputs until such time as optimisation has been performed to within one or more required thresholds or parameters, or until an output is manually selected.

The surgical plan, and other data produced by the system can be visualised to provide a human user such as a surgeon with images that can assist the surgical process and/or allow the user to visualise implant placement and the effects the implant may have on post-operative ranges of movement or other effects that may be experienced by the patient.

In some embodiments the model 104 may use machine learning to assist with predictive functions of the system. For example, the post-operative function assessment might be performed by model 104 based on post-operative data obtained from previous patients. Thus, a predicted post-operative assessment may be used as another input in determining the implant selection and placement.

In overview, the system 100 broadly provides a digitally implemented surgical planning system having:

1. Pre-operative patient function assessments 101 using wireless inertia motion/measurement unit (IMU) sensors.
2. An image processing sub-system 102 that uses deep neural networks to produce digital models of the patient's anatomy.
3. An implant selection and placement sub-system 103 that
   a. digitally fits a library of implants 118 to the outputs of 105
   b. displays the patient anatomy and implants
   c. allows a user to adjust the implant selection and placement
   d. Displays the patient's pre-operative functional metric, their predicted normal functional metric, and predicted post-operative functional metric.
4. A machine-learning/biomechanical hybrid model (the hybrid model) 104 that
   a. predicts the patient's functional metric given an initial or working surgical plan 113
   b. estimates the patient's current functional metric given motion data from 101
   c. predicts the patient's normal functional metric given motion data from 101
   d. learns from pre and post-operative functional data and patient anatomy data to improve its prediction of 4(*a*), (*b*), and (*c*).
5. A range of motion analysis sub-system 105 that compares the output of 104 and provides feedback to 103 for visualisation and optimisation of implant selection and placement.
6. Post-operative patient function assessments 106 using wireless inertia motion unit (IMU) sensors that is used to validate 4(*b*) and 4(*c*) and improve 4.
7. Post-operative range of motion analysis sub-system 107 that estimates actual post-operative functional metric.

Further aspects of the system 100 will be described in greater detail further below.

Referring to FIG. 3, more detail is provided as to how patient motion metrics are obtained and processed in some embodiments. Model 104 includes a kinematic model generator 201 that produces a digital functional model 204 of the required or subject patient anatomy from patient anatomy models 110 generated by the image processing sub-system (which is described further below). This model consists of anatomical structures including without limitation bones, joints, muscles and other features having geometric constraints adapted to the patient's anatomy that model the function of the patient's musculoskeletal system. The model generator 201 can optionally take as input a surgical plan 113 that includes one or more implants. In this example, the generator adjusts the joint geometry to replace the patient's own joint with the artificial joint.

A functional metric estimator 202 produces the functional metric from IMU data and the patient-specific kinematic model from 204 to provide estimated pre-operative functional metrics 205.

A functional metric predictor 203 that uses the kinematic model, patient medical images, estimated functional metrics from 205, raw patient motion data, and population models of anatomy and function 206 to predict the functional metric 207 of the patient if they had a normal joint (in the example of a joint replacement procedure). This predictor uses a combination of biomechanical models and machine-learning techniques to combine the various input data types for a prediction.

Turning to FIG. 4, more detail is provided as to how implant selection and placement is determined in some embodiments. The implant selection and placement subsystem 103 may include an implant fit simulator 401 that fits each implant in an implant library 118 to the patient's anatomical models 110 taking into account surgical constraints. The fit simulator 401 scores and then ranks each implant at step 406 based on how well it
   a. fits to the patient anatomy
   b. restores patient anatomy
   c. restores patient function The outputs of 401 are sent to a graphical user interface 402 which displays to a user (e.g. a surgeon). In some embodiments this allows the surgeon to perform one of more of the following:

View the patient anatomy and implants. In some embodiments this allows the surgeon to view the implant and/or implant and anatomical structures from one or more selected directions and/or distances, in cross-section, and/or with overlayed graphical and text data View graphical and textual representations of one or more of: the patient's measured function; predicted normal function; predicted post-operative function, and any measured post-operative function Modify the selection and placement of implants with real-time graphical feedback on the change and impact on post-operative patient anatomy and function Approve and finalise implant selection and placement to prevent further modification and to produce documentation of the surgery plan for implant procurement, intra-operative guidance, and post-operative review.

After user approval or modification, the selected implant(s) and their positioning are input to the hybrid biomechanical model 403 to predict the post-operative function (see above)

A range of motion analysis 405 is performed on the predicted normal function 2067 and the predicted post-operative function to calculate the difference at 408. In at least some embodiments the system 100 is configured to minimise difference 408, so this difference is sent to the fit simulator 401 to adjust implant positioning and scoring, and to the user interface 402 to give the user feedback on the performance of the selected implant(s).

Turning now to FIG. 5, one or more embodiments of the image processing sub-system 102 will now be described in more detail. The subsystem 102 may include a deep neural network (DNN) and a set of image filters 301 that generates 3D models of anatomical structures such as bones, muscles, and other relevant anatomical structures from one or more medical images 117 of the patient. The image or images may comprise 2-D X-ray, 3D X-ray CT, 3D MRI, or other modalities. The DNN is trained to associate input image texture with output 3D voxel volumes of the various anatomical structures. A series of image filters including thresholding, region-growing, gaussian smoothing, and marching-cubes then convert the 3D voxel volumes into 3D triangulated meshes. In some embodiments these raw geometric models or meshes 302 consist of arbitrary ordering of triangles and no information about anatomical regions or landmarks.

Sub-system 102 also includes statistical shape models (SSM) 303 which may be fitted to the raw meshes. The SSM morphs a canonical triangulation of each anatomical object to the raw mesh so that meshes of the patient's anatomy are obtained which are with consistent triangulation as shown at 304. This allows the system to map anatomical regions and landmarks onto the geometry as shown at 305, and automatically take morphometric measurements such as lengths, angles, areas, and volumes as shown at 306.

Referring now to FIG. 6, a general process flow for obtaining anatomical models and simulating implant fit according to an embodiment of the invention will be described. The process begins at 640 and the first step is acquisition or uploading of medical anatomical images at 641. A 3D model of the patient anatomy relevant to the procedure (e.g. a patient anatomical structure such as a bone or bones) occurs at 642, after which landmarks in the form of target surgical features for implant integration are identified on the bone or similar structures in the model at 643. A digital model of an implant from a library of implants can then be automatically or manually selected. The implant model has its own target surgical features which are already identified, or may be adjusted or identified dependent on the anatomical digital model. The fit between the anatomical and implant models is simulated in step 644. Assuming the fit is adequate, then the model is used to simulate patient function, for example range of joint movement, in step 645. If function is adequate, the planning can be completed at 646. If inadequate, then an alternative implant can be selected and simulated as indicated by path 647.

Referring now to FIG. 7, an overview of an embodiment of a pre-operative planning system is shown, generally referenced 750 is disclosed in the context of one example of implementation in a client-server environment. Information management system 15, in this embodiment represented as a server 752, communicates via a network 12 with client-side application 754 which may be executed by a machine 11.

The client-side application 754 may be used by a user, for example a surgeon planning an orthopedic procedure, to open a new surgical case and upload patient anatomical images, as shown in block 755. In some embodiments, the anatomical images may be sourced from a variety of different medical imaging modalities, for example, X-ray, CT or MRI. Some modalities may be provided as 2D images, for example X-ray sourced images. Others may be 3D (or consist of a stack of 2D images that can be represented as a 3D image) for example sourced by CT or MRI. The client-side application provides the images to the server 742 as 2D images 756 or 3D images 757.

An image processing application running on the server then performs a 3D reconstruction of the patient anatomy from the images 756, 757 as shown in block 758, to automatically generate 3D model of the patient anatomy. The anatomy which is modelled will include the anatomical region which is the subject of the procedure, for example a hip or shoulder or knee.

The 3D model generated in block 758 is provided as a digital model in a format (such as STL, PLY, OBJ, or other formats) which can readily be provided back to the client side application 754 as shown in block 760 to enable the user to readily visualise the patient anatomy and manipulate the representation appearing on the client side device so that the user can obtain an adequate visualisation of all parts of the patient anatomy relevant to the intended procedure.

To generate the 3D model, the application represented by block 758 may make use of an additional tool such as an artificial neural network 759 which in some embodiments may comprise one or more deep neural networks.

The server 752 may also include a database 761 comprising a collection of statistical shape models (SSMs) of patient anatomy (e.g. bones, or other tissues and structures) which may be used to generate or reconstruct the 3D model.

In some embodiments, the 3D anatomical model is produced or reconstructed from 2D input medical anatomic images 756 by firstly using deep neural network 759 to identify selected landmarks which may comprises certain geometric features such as the volumes, regions, contours, or discrete points in the images belonging to the anatomical object.

Examples of the landmarks or geometric features can be seen with reference to FIG. 8A-D which are sketches using the hip joint as an example, in particular the Femoral head 801 as located next to or within the Acetabulum 802. FIG. 8A shows a geometric feature comprising the volume 803 (which is shaded) of the femoral head. FIG. 8B shows a region 804 (which is shaded) of the femoral head occupied by a plane in cross section. FIG. 8C shows a contour 805 (which is shown in broken outline) of the femoral head in a plane in cross section. FIG. 8D shows identified points 806 on the femoral head.

The next step is to fit an SSM of the related anatomical structure to the landmarks or contours to thus reconstruct a 3D model of the bone.

In some embodiments, the 3D anatomical model is produced or reconstructed from 2D input medical anatomic images 756 by using deep neural network 759 to directly predict the parameters of an SSM of a bone from one or more medical images. The predicted parameters can then be used to generate a 3D model of the bone from the SSM.

In some embodiments, the 3D anatomical model is produced or reconstructed from a 3D image volume (for example composed of a set of 2D CT or MRI images), such as input medical anatomic images 757, by using deep neural network 759 to identify and label the relevant regions of bones of interest from the 3D image volume.

Where using input 2D or 3D images, the identified volume, region, contour, or points may encompass or be on a single connected portion of one object (e.g. part of one bone), multiple unconnected regions of one object (e.g. different pieces of a fractured bone), or multiple objects (e.g. all the bones that make up a joint (e.g. the femur, tibia, and patella in the knee) or larger structure (e.g. multiple vertebrae that make up the spine).

Having produced a patient 3D anatomical model, the next step is to identify landmarks in the form of target surgical features for implant integration on the bone (or similar structures) in the model 3. These target surgical features or regions are mapped onto the patient 3D models using an SSM. This can be achieved by:
  i. producing a canonical representation of a 3D geometry (e.g. a triangulated mesh of a bone) that includes a mean shape and a description of the modes of variation of that mean shape observed in a population (e.g. the variation in shape of a bone across a human population); or
  ii. An SSM's canonical representation can be customised to the shape of a particular individual by morphing the mean shape according to the modes of variation, each weighted by a different score; or
  iii. An SSM can be fitted to an individual's shape by
  Describing the individual's shape as a point cloud (e.g. from image segmentation)
  Morphing the mean shape of the SSM according to its modes of variation by optimising the scores of the modes of variation to minimise some cost function (e.g. sum of the squared distance between the point cloud and the morphed shaped). This produced an approximation of the individual shape that will still have significant differences in some regions
  Further morph the previously morphed SSM mesh by using a finer scale deformation function to further minimise the cost function from above. An example of such a finer-scale deformation function is a set of radial basis function. The final morphed mesh is within 1 mm RMS of the individual's shape.

The SSM of each bone (or other structure) contains additional information about anatomical points, regions, axes, and other geometric features on the canonical geometry (e.g. triangulated mesh), for example spheres, cylinders cones best fitted to the platform. Examples are shown in FIGS. 9A and B, in which sketches of a femur 900 are shown marked up with reference to the landmarks, regions and features described below.
  i. An anatomical landmark 901 can be described by the index of the mesh vertex that is closest to the landmark
  ii. An anatomical region 902 is described by the set of indices of the mesh vertices and faces that fall within the region
  iii. An additional feature is an anatomical axes 903 defined by a line between two landmarks, a line fitted through 3 or more landmarks, a line or axis 904 fitted through a region, or a line fitted through a combination of landmarks and regions.
  iv. An additional feature is a circle with a centre and radius fitted to three or more anatomical landmarks and/or a region.
  v. An additional feature is a sphere 907 with a centre 905 and radius 906 fitted to four or more anatomical landmarks and/or a region.
  vi. An additional feature is a plane 908 with an in-plane point and a normal vector calculated from two landmarks or fitted through a region
  vii. An additional feature is a local cartesian coordinate system with an origin point and three orthogonal vectors calculated by at least 3 landmarks, or a combination of landmarks, axes, and planes.
  viii. Other geometric features are also possible.
  c. When such an SSM is morphed to the segmented surface of a bone, the anatomical landmarks and regions on the SSM mean mesh are morphed along to the segmented surface.
  d. The morphed mesh now becomes an accurate representation of the patient's bone shape that is annotated with the locations of their anatomical landmarks, regions, and features. These landmarks, regions, and features provide targets and constraints for the fitting of implants.

Having produced an anatomical digital model of the patient anatomy that has identified surgical target landmarks or regions, the next step is to select an implant from the library of implant shapes and sizes and simulate implant fit from the selected implant, or simply perform simulation across the library of implant shapes and sizes.
  a. Simulation involves the optimisation of fit between predefined regions on the implant geometry and regions on the patient anatomy.
  b. The fit is between an implant 3D model and the morphed structural (e.g. bone) model from the step above.
  c. Just like the bone model, the implant model is also annotated with landmark points and regions
  d. Depending on the bone, and the type, brand, size, or variant of the implant, different regions and landmarks are used as objectives or constraints in the fitting simulation. E.g.
    i. Regions to optimise for contact
    ii. Regions to optimise for non-contact
    iii. Points to minimise distance to
    iv. Points to maximise distance to
    v. Region, plane, sphere or other geometric feature to using in fitting objective or constraint
  e.g. for fitting cementless femoral stems to the femoral canal in a total hip replacement:
    I. Maximise the area of contact between the medial and lateral calcar regions of the stem and the femoral canal Minimise the distance between the tip of the femoral stem and a point at the centre of the femoral canal mid-way along the femoral shape.
    iii. Minimise the angle between the femoral neck angle and the stem neck angle
    iv. Plus other rules
  f. After the simulation, the quality of the fit is quantified by calculating a score based on one or more geometric and/or functional measurements between the implant and the bones. E.g. the change in leg length before and after the fit of the implant, or the range of joint motion.
  g. Landmarks and other features on the fitted implant is used to define geometries (e.g. planes, spheres, cuboids) that are then used to simulate the resection (cutting) of the bone required to deliver the implant operatively.

The system 100 allows simulation of patient function with their native and implanted anatomy a. The anatomical landmarks and regions on the morphed bone models and implant models are used to construct joint coordinate systems between adjacent bones (e.g. femur and pelvis).
b. Native function is concerned with the relative motion of un-implanted bone models
c. Implanted function is concerned with the relative motion of models that are the combination of fitted implants and resected bones.
d. The function of the patient anatomy is determined by the ability of their bone and implant models to move freely relative to each other as governed by their joint coordinate systems.
e. Moving freely is defined by
f. Moving 3D models not coming with contact or some defined distance to other 3D models.
3D models having the ability to move relative to another as governed by biomechanical models of passive and active forces provided by muscles, tendons, ligaments, and other anatomical structures, as well mass, inertia, and other physical properties.
f. Furthermore, function can be defined by the joint to move freely to achieve the motion required for a function task, e.g. standing up, walking, reaching, grabbing, arm swinging.

Figure 10:
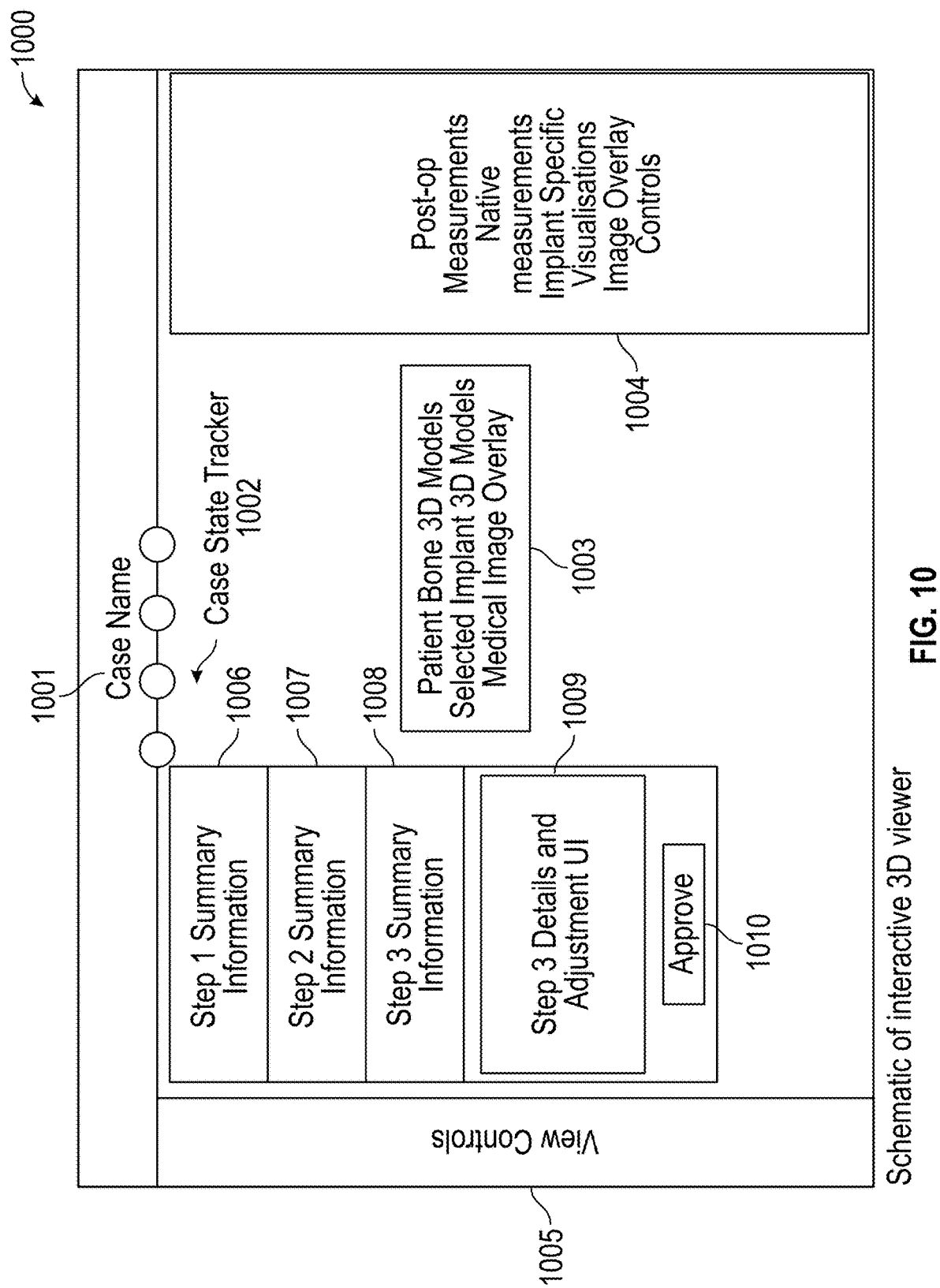
Figure 11:
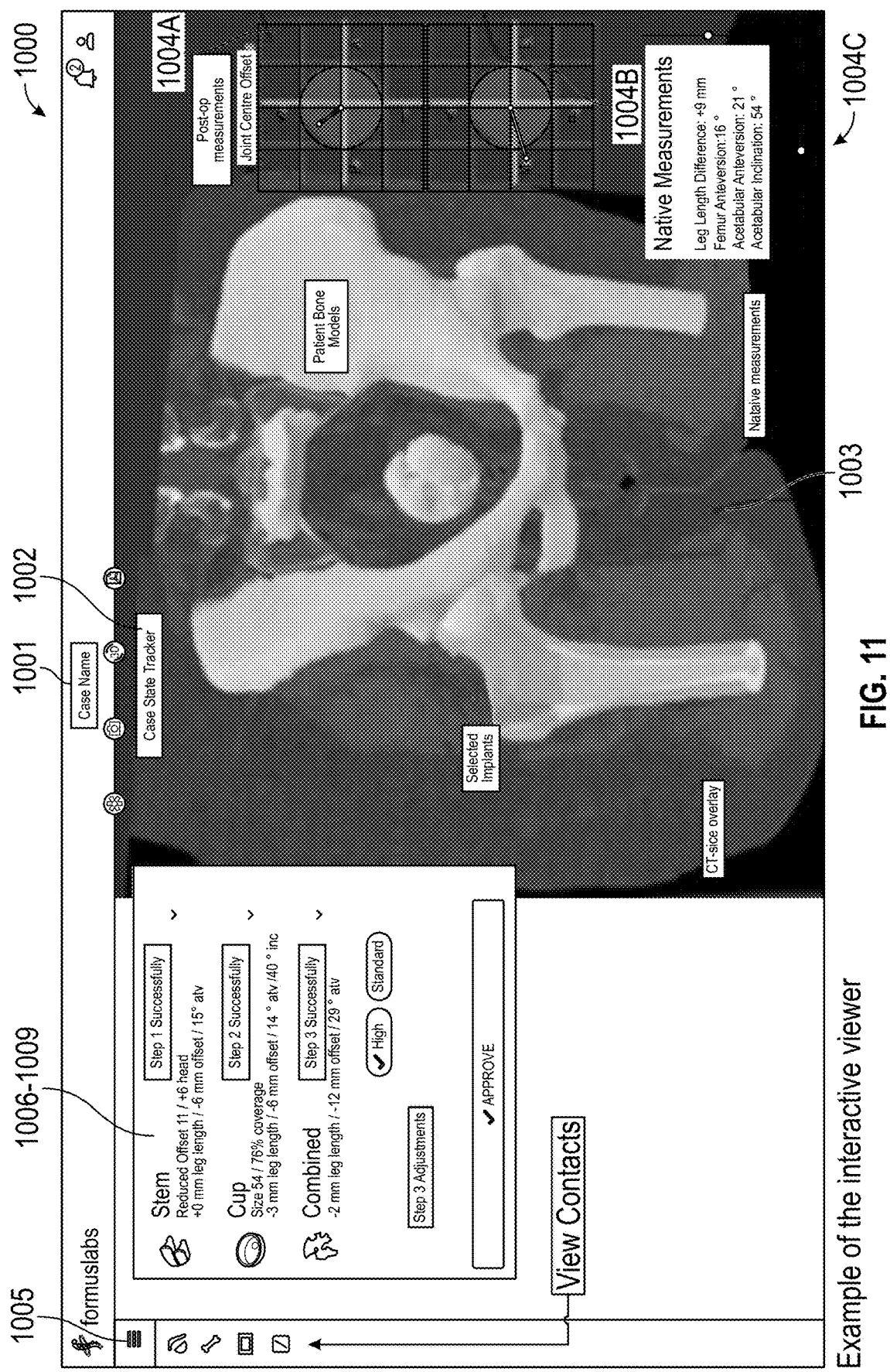
Figure 12:
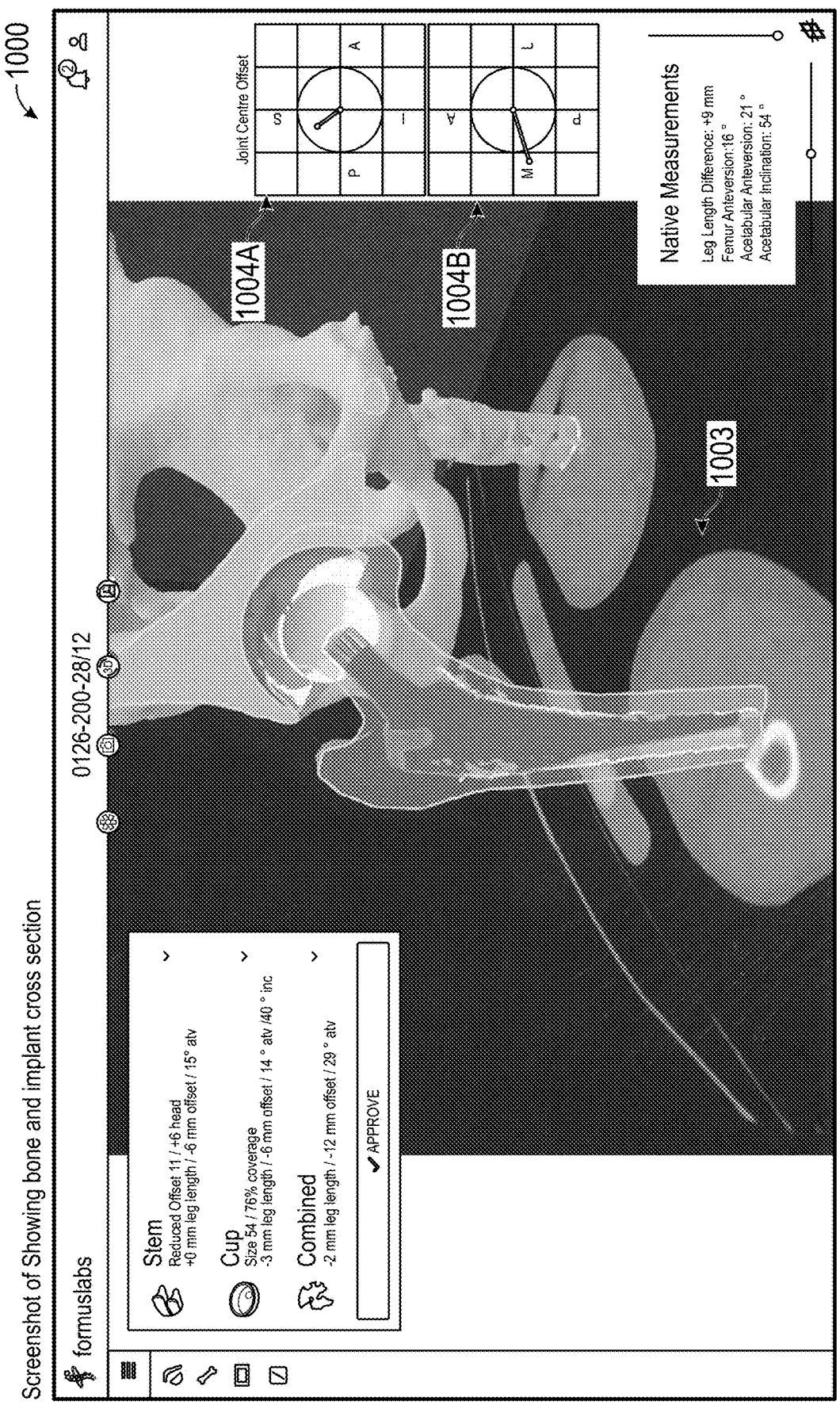
Figure 13:
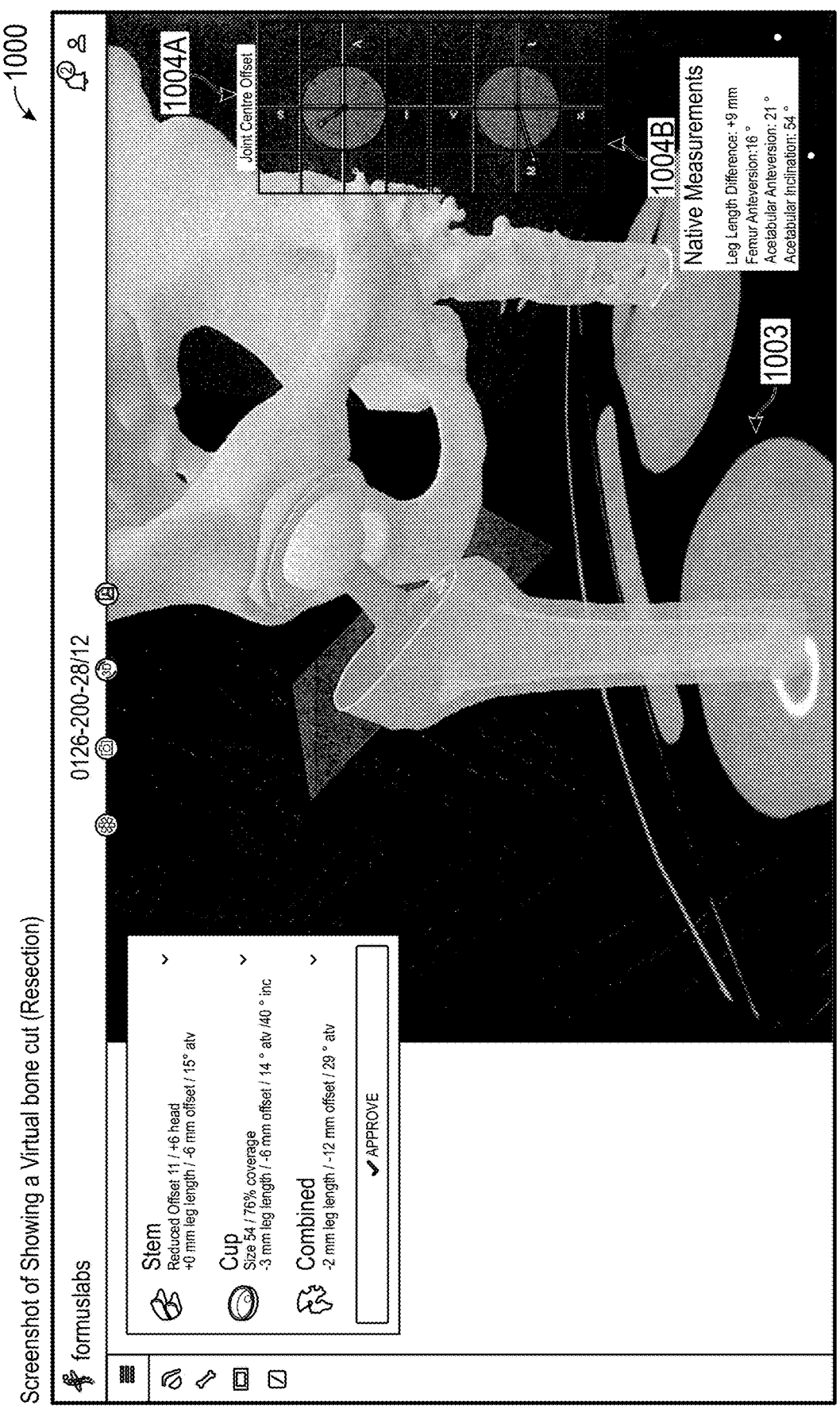
Figure 14:
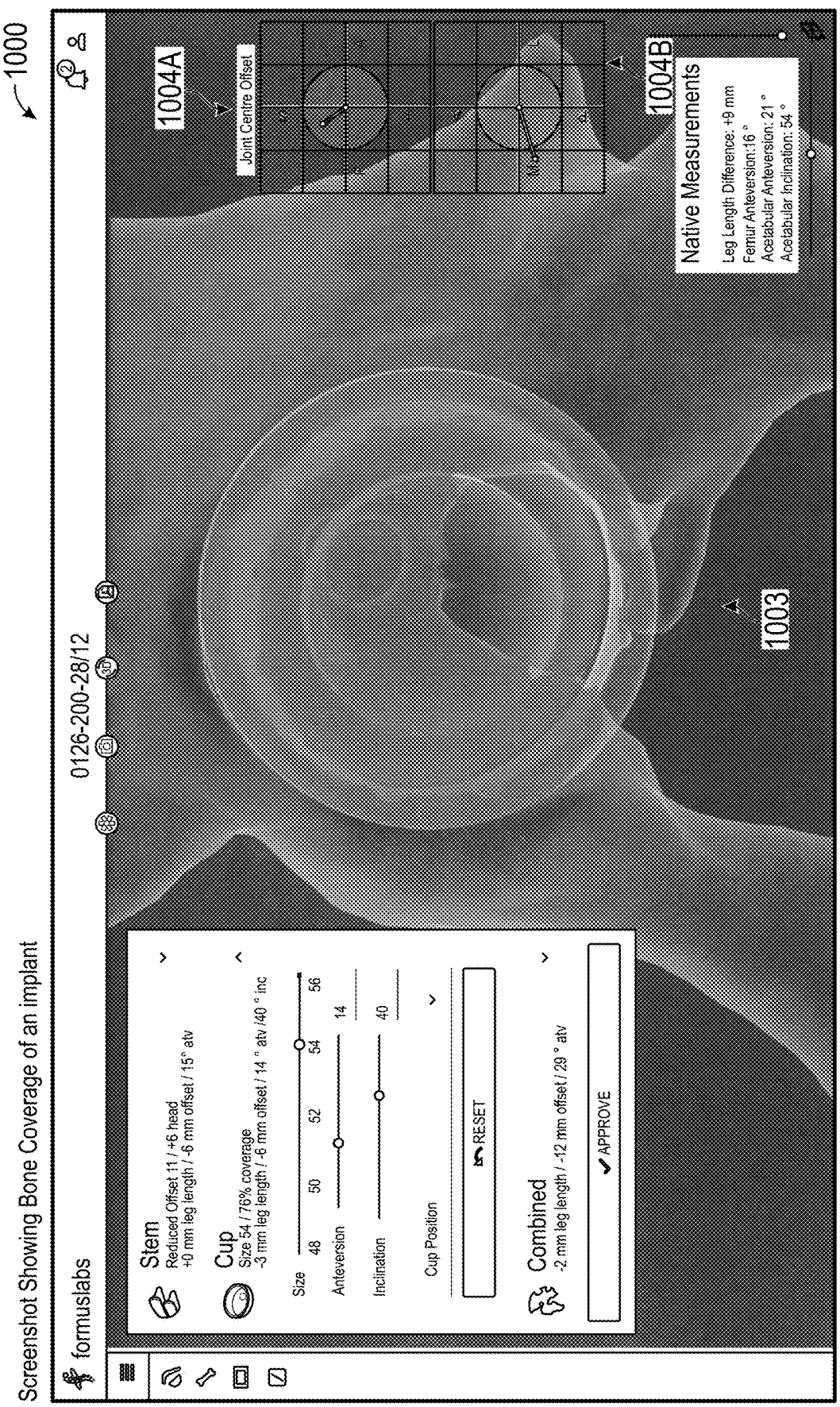
Figure 15:
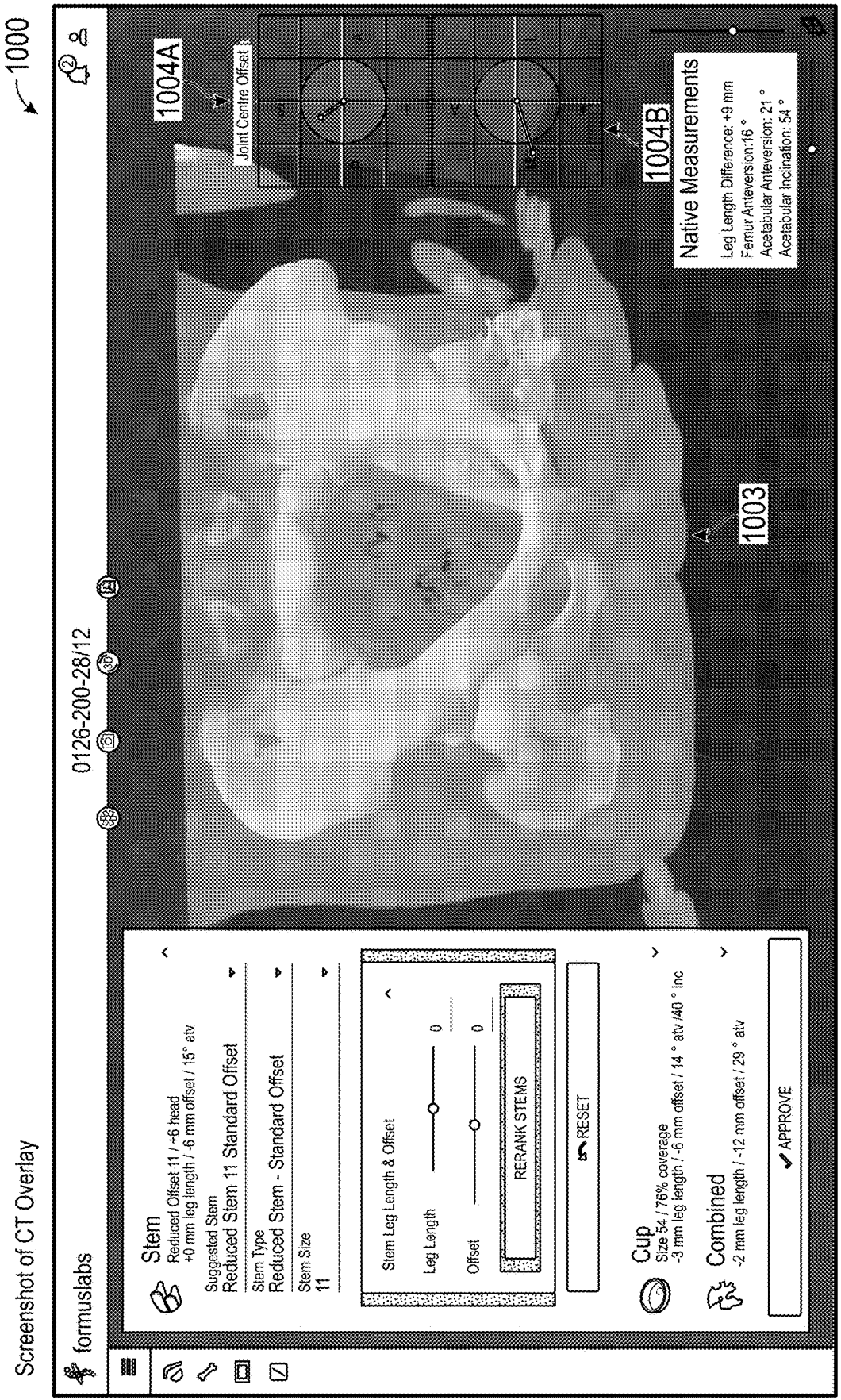
Figure 16:
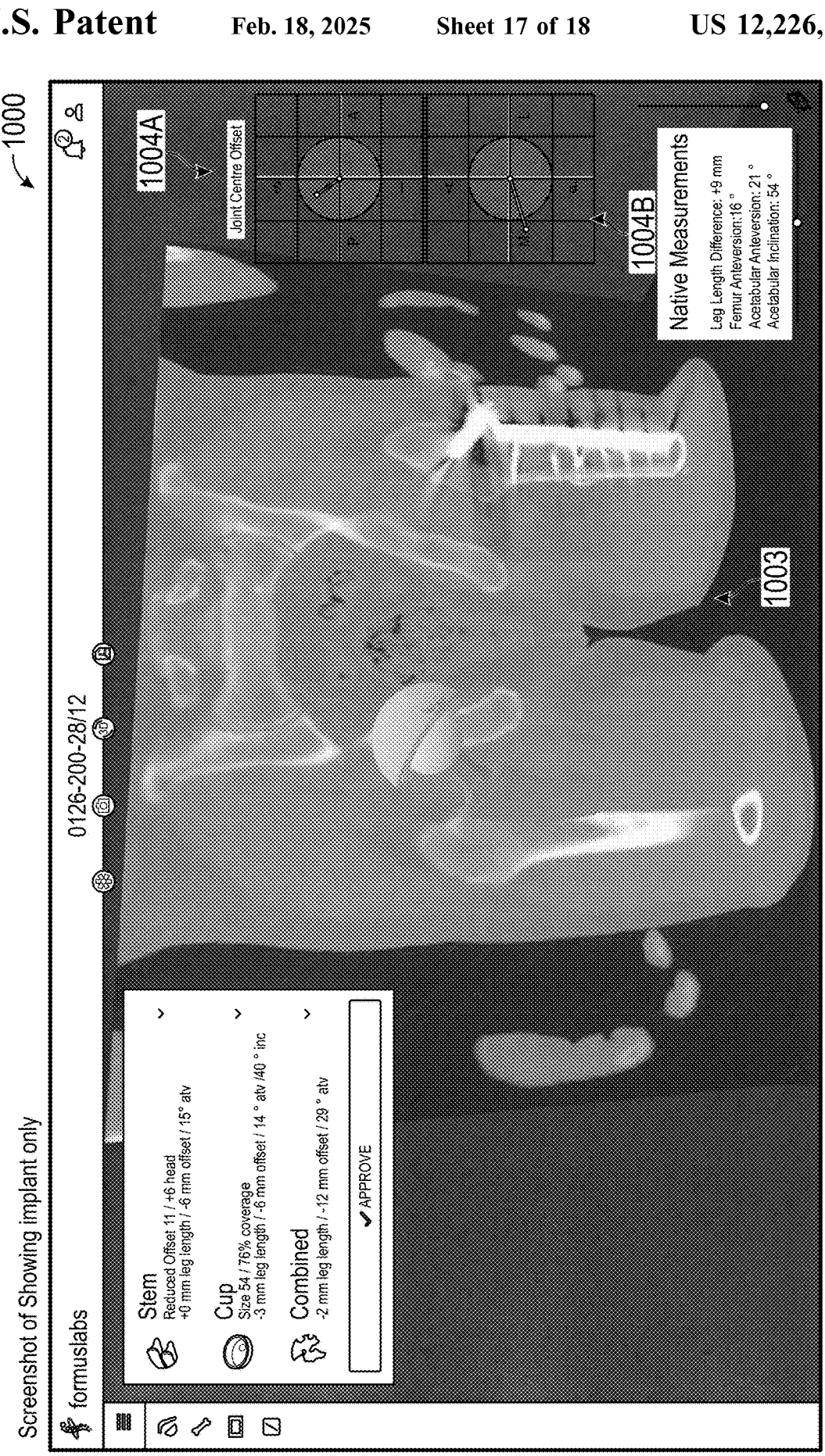
Figure 17:
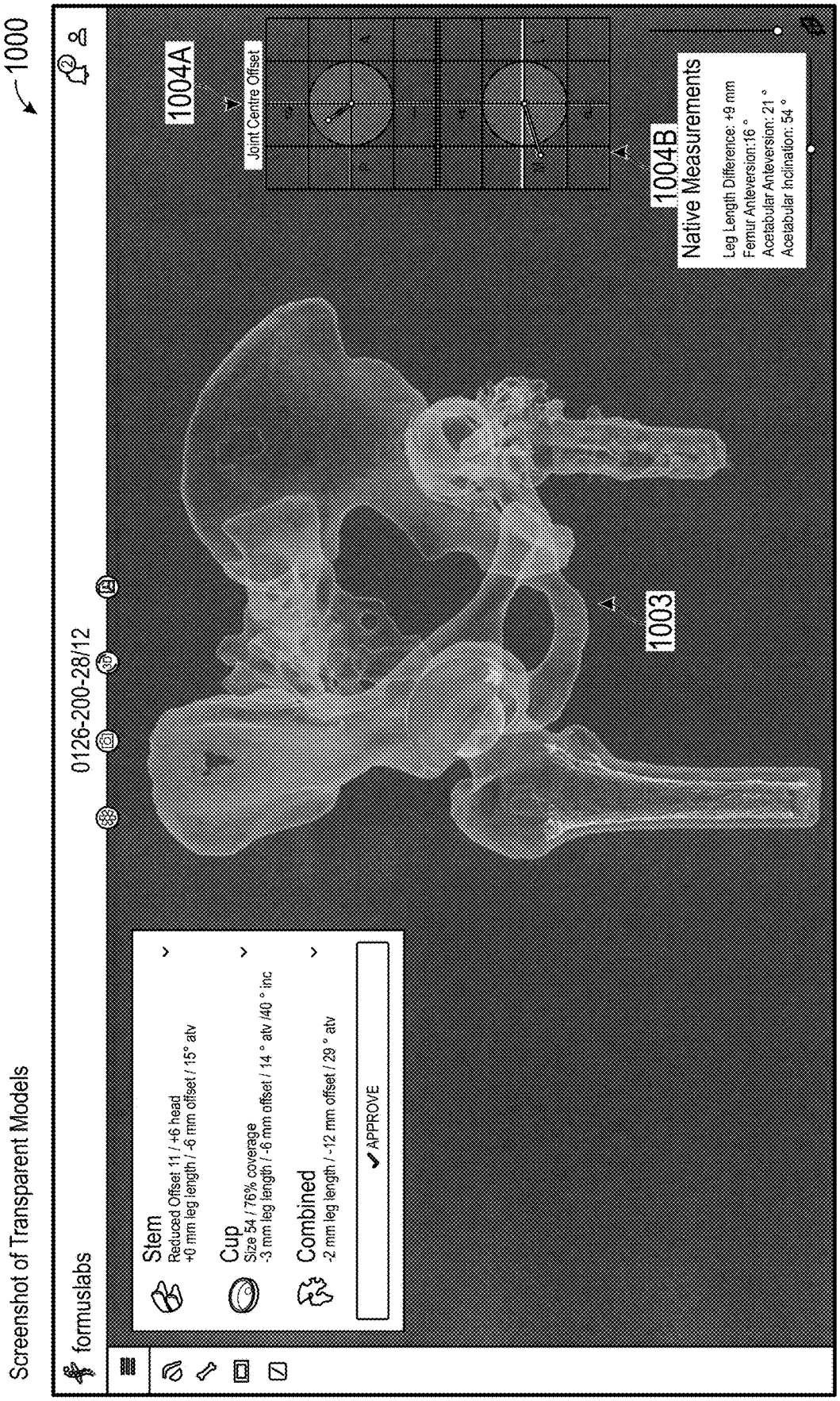

As mentioned above, the system 100 includes a user interface which is shown in FIGS. 10-17. As can be seen in FIG. 10, a graphical user interface 1000 has a case identifier field 1001 beneath which case state tracker 1002 is provided. The case state tracker allows the user to immediately recognise the case status, including without limitation whether the pre-operative plan is complete, whether surgery has been performed and whether post-operative assessment has been completed.

Controls 1005 include control elements configured to allow the user to make manual adjustments at various stages of the planning process, or to allow the system to perform steps automatically. Summary information on each step is provided in fields 1006-1009 and these may include graphical control elements to allow the user to navigate to processes involved in some or multiple steps and/or use controls 1005 to implement changes in implant selection or positioning for example. An approval or sign-off button 1010 allows user or supervisor approval of the plan produced by the system, or alternatively approval for selected steps in the process.

As can be seen, a field or window 1003 is provided in which a display of a 3D model of the patient anatomy and of simulated implant (in this example) fit on the 3D model is portrayed. The display or visualisation in window 1003 is able to be manipulated by the user, and this is shown by way of example in FIGS. 11-17. The display shows patient function pre and post implantation, allows the user to select implants based on simulation results and adjust implant position and orientation. Furthermore, the user is informed of in real-time of quantitative changes to implant fit as they make adjustments.

Post-operative measurements, native measurements, implant specific visualisations and image overlay controls are provided in field or window 1004. Significantly, this window provides a multiaxis visualisation of joint centre offset—in multiple planes as shown in 1004A and 1004B in FIG. 11, with one plane showing joint offset in the posterior-anterior and superior-Inferior axes, and the other plane showing joint offset in the medial-lateral and posterior-anterior axes. Reference numerals are omitted from FIGS. 12-17 for clarity.

The processes and systems described herein may be performed on or encompass various types of hardware, such as computer systems. In some embodiments, computer, display, and/or input device, may each be separate computer systems, applications, or processes or may run as part of the same computer systems, applications, or processes—or one of more may be combined to run as part of one application or process—and/or each or one or more may be part of or run on a computer system. A computer system may include a bus or other communication mechanism for communicating information, and a processor coupled with the bus for processing information. The computer systems may have a main memory, such as a random access memory or other dynamic storage device, coupled to the bus. The main memory may be used to store instructions and temporary variables. The computer systems may also include a read-only memory or other static storage device coupled to the bus for storing static information and instructions. The computer systems may also be coupled to a display, such as a CRT or LCD monitor. Input devices may also be coupled to the computer system. These input devices may include a mouse, a trackball, or cursor direction keys.

Each computer system may be implemented using one or more physical computers or computer systems or portions thereof. The instructions executed by the computer system may also be read in from a computer-readable medium. The computer-readable medium may be a CD, DVD, optical or magnetic disk, laserdisc, carrier wave, or any other medium that is readable by the computer system. In some embodiments, hardwired circuitry may be used in place of or in combination with software instructions executed by the processor. Communication among modules, systems, devices, and elements may be over a direct or switched connection, and wired or wireless networks or connections, via directly connected wires, or any other appropriate communication mechanism. The communication among modules, systems, devices, and elements may include handshaking, notifications, coordination, encapsulation, encryption, headers, such as routing or error detecting headers, or any other appropriate communication protocol or attribute. Communication may also messages related to HTTP, HTTPS, FTP, TCP, IP, ebMS OASIS/ebXML, secure sockets, VPN, encrypted or unencrypted pipes, MIME, SMTP, MIME Multipart/Related Content-type, SQL, etc.

Any appropriate 3D graphics processing may be used for displaying or rendering including processing based on WebGL, OpenGL, Direct3D, Java 3D, etc. Whole, partial, or modified 3D graphics packages may also be used, such packages including 3DS Max, SolidWorks, Maya, Form Z, Cybermotion 3D, Blender, or any others. In some embodiments, various parts of the needed rendering may occur on traditional or specialized graphics hardware. The rendering may also occur on the general CPU, on programmable hardware, on a separate processor, be distributed over multiple processors, over multiple dedicated graphics cards, or using any other appropriate combination of hardware or technique.

As will be apparent, the features and attributes of the specific embodiments disclosed above may be combined in different ways to form additional embodiments, all of which fall within the scope of the present disclosure. Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not 5 generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Any process descriptions, elements, or blocks in the flow diagrams described herein and/or o depicted in the attached figures should be understood as potentially representing modules, segments, or portions of code which include one or more executable instructions for implementing specific logical functions or steps in the process, such as functions referred to above. Alternate implementations are included within the scope of the embodiments described herein in which elements or functions may be deleted, executed out of order from that shown or discussed, including 5 substantially concurrently or in reverse order, depending on the functionality involved, as would be understood by those skilled in the art.

All of the methods and processes described above may be embodied in, and fully automated via, software code modules executed by one or more general purpose computers or processors, such as those computer systems described above. The code modules may be stored in o any type of computer-readable medium or other computer storage device. Some or all of the methods may alternatively be embodied in specialized computer hardware.

It should be emphasized that many variations and modifications may be made to the above-described embodiments, the elements of which are to be understood as being among other acceptable examples. All such modifications and variations are intended to be included herein within 5 the scope of this disclosure and protected by the following claims.

The present invention has been described above with reference to specific embodiments. However, other embodiments than the above described are equally possible within the scope of the invention. Different method steps than those described above, performing the method by hardware or software, may be provided within the scope of the invention. The different features and steps of the invention may be combined in other combinations than those described. The scope of the invention is only limited by the appended patent claims.

The invention claimed is:

1. A method for determining one or more of selection, positioning or placement of a surgical implant, the method including the steps of:
    obtaining pre-operative data regarding an impaired anatomical structure of a patient;
    producing a patient anatomical model;
    predicting, using the obtained pre-operative data and the produced patient anatomical model, function of the anatomical structure in an unimpaired condition;
    predicting post-operative function of the structure for one or more implants;
    performing a range of motion analysis on the predicted unimpaired function and the predicted post-operative function to calculate one or more differences and minimising the one or more differences between the predicted post-operative function and the predicted unimpaired function; and
    selecting one or more of the implants, positions of the one or more implants or locations of the one or more implants to improve the predicted post-operative function.

2. The method of claim 1, wherein data for the subject or patient of the one or more implants or data for a population of subjects is obtained.

3. The method of claim 1, wherein post-operative data is obtained to improve the predictive functions.

4. The method of claim 1, further comprising producing a patient anatomical model.

5. The method of claim 4, wherein the model comprises a 3D model.

6. The method of claim 4, wherein the patient anatomical model is generated from one or more patient medical images.

7. The method of claim 6, wherein one or more patient medical images is processed and a statistical shape model is used to produce the patient anatomical model.

8. The method of claim 7, further comprising using a machine learning method to classify or filter the patient medical images or patient anatomical images.

* * * * *